United States Patent
Vitzrabin et al.

(10) Patent No.: US 11,511,423 B2
(45) Date of Patent: Nov. 29, 2022

(54) METHOD OF PLOTTING ULTRAVIOLET (UV) RADIATION FOR DISINFECTION

(71) Applicant: UVD Robots Aps, Odense (DK)

(72) Inventors: Efraim Vitzrabin, Odense (DK); Rune K. Larsen, Odense (DK); Thomas Rubaek, Odense (DK); John Erland Østergaard, Odense (DK)

(73) Assignee: UVD Robots ApS, Odense (DK)

( * ) Notice: Subject to any disclaimer, the term of this patent is extended or adjusted under 35 U.S.C. 154(b) by 261 days.

(21) Appl. No.: 16/836,153

(22) Filed: Mar. 31, 2020

(65) Prior Publication Data
US 2021/0299868 A1 Sep. 30, 2021

(51) Int. Cl.
*B25J 9/16* (2006.01)
*A61L 2/10* (2006.01)
(Continued)

(52) U.S. Cl.
CPC ......... *B25J 9/1664* (2013.01); *A61L 2/10* (2013.01); *B25J 9/161* (2013.01); *B25J 9/1692* (2013.01); *B25J 9/1694* (2013.01); *B25J 11/0085* (2013.01); *B25J 13/087* (2013.01); *B25J 19/04* (2013.01)

(58) Field of Classification Search
CPC .............. B25J 9/16; B25J 11/00; B25J 13/08
See application file for complete search history.

(56) References Cited

U.S. PATENT DOCUMENTS 7,805,220 B2 9/2010 Taylor
8,779,391 B2 7/2014 Flaherty
(Continued)

FOREIGN PATENT DOCUMENTS

AU 2013368082 B2 7/2015
CN 103959429 A 7/2014
(Continued)

OTHER PUBLICATIONS

Baker, "UV Bacteria-Killing Robot Cleans Hospital Rooms far Better than Humans", Interesting Engineering, Inc., Jun. 28, 2018, URL:https://interestingengineering.com/uv-bacteria-killing-robot-cleans-hospital-rooms-far-better-than-humans, 16 pages.
(Continued)

*Primary Examiner* — Kira Nguyen
(74) *Attorney, Agent, or Firm* — Kevin Roddy; Butzel Long

(57) ABSTRACT

Implementations of the disclosed subject matter provide a method of moving, using a drive system, a mobile robot within an area. Detecting, using at least one sensor of the mobile robot, at least one of air within the area, a surface within the area, and/or an object within the area. The area may be mapped in three dimensions based on the detecting of at least one of the air, the surface, and the object as the mobile robot moves within the area. Ultraviolet (UV) light may be emitted from a light source of the mobile robot to disinfect at least a portion of the area. A representation of the emission of the UV light may be plotted onto the mapped area to generate an exposure plot, where the representation is of the UV light emitted on at least one of the air, the surface, and the object in the area.

14 Claims, 12 Drawing Sheets

(51) Int. Cl.
  *B25J 11/00* (2006.01)
  *B25J 13/08* (2006.01)
  *B25J 19/04* (2006.01)

(56) References Cited

U.S. PATENT DOCUMENTS

| | | | |
|---|---|---|---|
| 8,932,535 B2 | 1/2015 | Hyde | |
| 2012/0125363 A1* | 5/2012 | Kim | A47L 9/2805 134/6 |
| 2014/0330452 A1* | 11/2014 | Stewart | B25J 19/02 701/2 |
| 2016/0271803 A1* | 9/2016 | Stewart | B25J 11/0085 |
| 2018/0193502 A1* | 7/2018 | Ufkes | A61B 90/70 |
| 2018/0339075 A1* | 11/2018 | Kennedy | A61L 2/24 |
| 2019/0015985 A1 | 1/2019 | Kim | |
| 2019/0117812 A1* | 4/2019 | Olsen | A61L 2/26 |
| 2019/0202057 A1 | 7/2019 | Smith | |
| 2020/0009280 A1* | 1/2020 | Kupa | A61L 9/20 |
| 2021/0046650 A1* | 2/2021 | Deyle | G05D 1/0214 |

FOREIGN PATENT DOCUMENTS

| | | |
|---|---|---|
| CN | 109568623 A | 4/2019 |
| DE | 102008064251 A1 | 7/2010 |
| KR | 101724447 | 4/2017 |
| TW | 201902561 A | 1/2019 |
| WO | 2018132679 A1 | 7/2018 |
| WO | 2019079065 A1 | 4/2019 |
| WO | 2019159162 A1 | 8/2019 |

OTHER PUBLICATIONS

Ansaldo, "How a robot vacuum navigates your home", News, Jul. 2, 2018, https://www.techhive.com/article/3281014/how-a-robot-vacuum-navigates-your-home.html, 8 pages.

Notice of Allowance issued in App. No. EP20167743.2, dated Jul. 1, 2022, 40 pages.

Chinese Office Action issued in App. No. CN202010288991, dated Aug. 9, 2022, 6 pages.

Taiwanese Office Action issued in App. No. TW109111632, dated May 12, 2022, 5 pages.

\* cited by examiner

DISINFECTION REPORT

- Amount of Area Disinfected (based on the exposure plot) = 100%

- Number of Objects detected Area = 7

- Percentage of Number of Objects Disinfected = 100%

- Number of reference tags that have a Changed State = 4

METHOD OF PLOTTING ULTRAVIOLET (UV) RADIATION FOR DISINFECTION

BACKGROUND

Mobile devices, such as mobile robots, can be operated so as to disinfect areas of a room, such as a floor, that have an unclean surface. Typically, it is difficult to determine whether such mobile devices have disinfected all contaminated surfaces, or whether the disinfection has been effective.

BRIEF SUMMARY

According to an implementation of the disclosed subject matter, a method may include moving, using a drive system, a mobile robot within an area. The method may include detecting, using at least one sensor of the mobile robot, at least one of air within the area, a surface within the area, and/or an object within the area. The method may map, using a processor communicatively coupled to the at least one sensor, the area in three dimensions based on the detecting of at least one of the air, the surface, and the object as the mobile robot moves within the area, or the method may use an existing 3D mapping of the area stored in a memory communicatively coupled to the processor. A light source of the mobile robot may emit ultraviolet (UV) light to disinfect at least a portion of the area, including the at least one of the air, the surface, and the object, where the emitting may be performed during at least one of: when the mobile robot is within the area, as the mobile robot moves within the area, before the mapping of the area, during the mapping of the area, and/or after the mapping of the area. The method may include, plotting, using the processor, a representation of the emission of the UV light onto the mapped area to generate an exposure plot, wherein the representation is of the UV light emitted on at least one of the air, the surface, and the object in the area.

Additional features, advantages, and implementations of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate implementations of the disclosed subject matter and together with the detailed description serve to explain the principles of implementations of the disclosed subject matter. No attempt is made to show structural details in more detail than may be necessary for a fundamental understanding of the disclosed subject matter and various ways in which it may be practiced.

FIG. 7 shows an example disinfection report according to an implementation of the disclosed subject matter.

DETAILED DESCRIPTION

Figure 1:
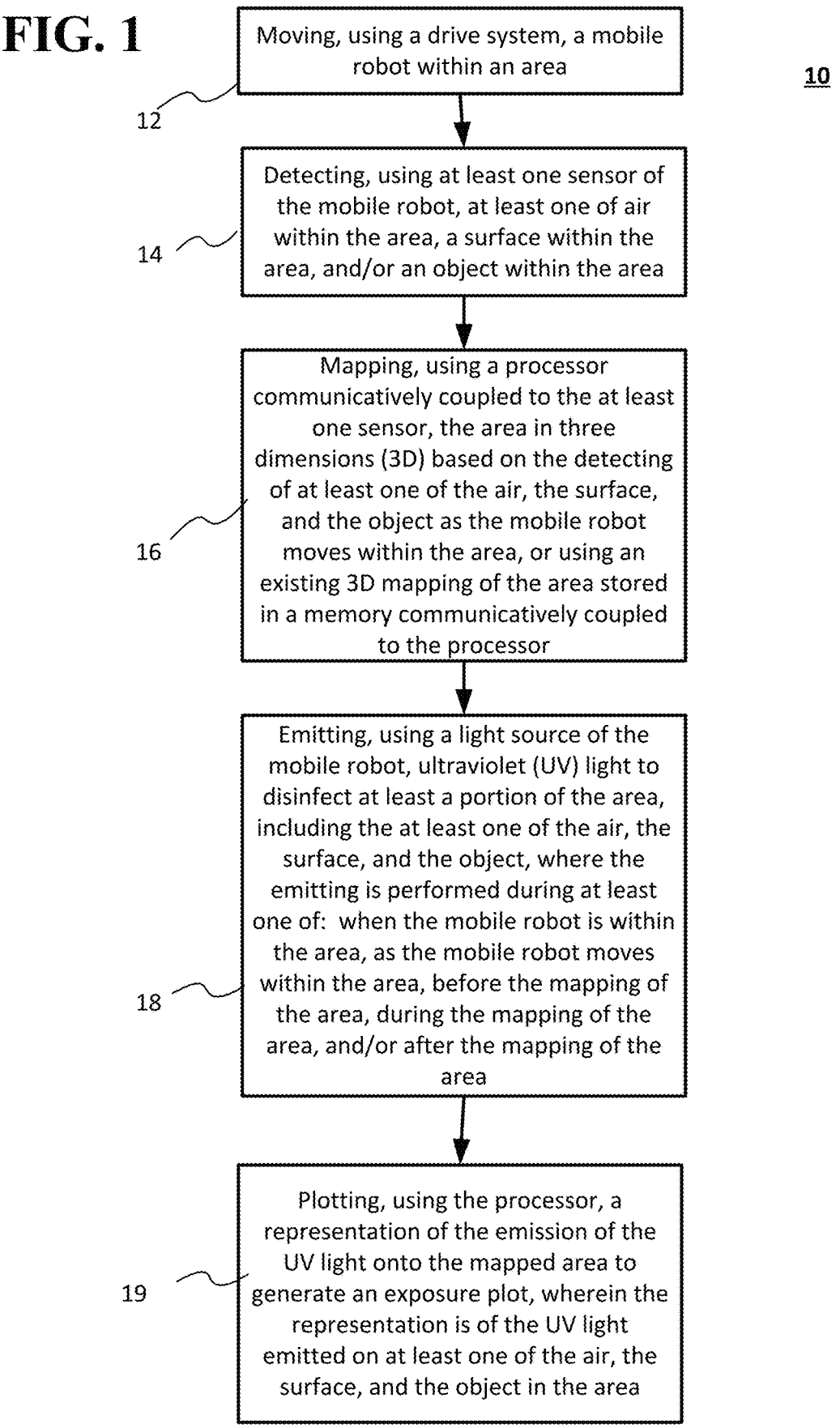
FIG. 1 shows an example method of plotting a representation of ultraviolet (UV) light emitted from a light source of a mobile robot to disinfect an area according to an implementation of the disclosed subject matter.

In implementations of the disclosed subject matter, one or more sensors of a mobile robot may detect air, a surface, an object, or the like in an area as the mobile robot moves within the area. A processor of the mobile robot may map the movement of the robot within the area, and/or the location of the surfaces and/or objects with the area. In some implementations, the processor may use an existing three dimensional (3D) mapping of the area that is stored in a memory that is communicatively coupled to the processor. The mobile robot may emit ultraviolet (UV) light from a UV light source. The UV light output by the light source may be used to disinfect air, a surface, an object, at least a portion of a room, and/or the area, or the like. The UV light may be output when the mobile robot is within the area, as the mobile robot moves within the area, before the mapping of the area, during the mapping of the area, and/or after the mapping of the area. The processor of the mobile robot may plot a representation of the emission of the UV light as an exposure plot. A disinfection report may be generated, which may indicate the amount of the area disinfected, the percentage of the objects and/or surfaces disinfected, and the like.

The mobile robot may be used as part of a regular cleaning cycle of a room, building, or the like, and may prevent and/or reduce the spread of infectious diseases, viruses, bacteria, and other types of harmful organic microorganisms in the environment by breaking down their DNA-structure with UV light. The mobile robot may reduce human error in cleaning an area, room, building, or the like by tracking the location and/or intensity (e.g., optical power of UV light) of light radiated, and determine which areas may need to be radiated and/or cleaned.

The mobile robot may be operated manually, autonomously, and/or may receive control signals to control the movement of the mobile robot with a room, building, area, or the like when operating in a tele-operation mode.

Traditional disinfection methods and devices using ultraviolet light require that a person enter a room or area with the device. With such methods and devices, the person may introduce new contaminants to the room or area. Other methods and devices use disinfectants such as wipes, chemicals, and the like. However, airborne particles may settle on the surface treated with the wipes and/or chemicals.

Implementations of the disclosed subject matter may deploy the mobile robot to a room, building, and/or area without putting a person (e.g., a member of a healthcare staff) at risk in a contaminated environment. That is, the mobile robot may disinfect air, surfaces, and/or objects without putting a member of the healthcare staff at risk, may reduce the costs of protective equipment for a person, may reduce time in disinfecting, and/or may provide a report which includes details of the surfaces and/or objects that have been disinfected.

In implementations of the disclosed subject matter, a mobile robot may enter a room, building, and/or area and perform disinfection operations using UV light. The mobile robot may move about the room, building, and/or area to generate a three dimensional (3D) map using at least one sensor that may be a 3D camera, a stereo camera, time-of-flight camera, structured light camera, a 3D LiDAR (Light Detection and Ranging) sensor, and/or a radar sensor (radio detection and ranging). In some implementations, the mobile robot may use an existing 3D mapping of the area stored in a memory of the mobile robot, and/or received by a communications interface from a server, a database, and/or remote platform where the map may be stored.

The mobile robot may include a wheel encoder and an IMU (inertial measurement unit) that may be included in a drive system that may be used to map the room, building, and/or area. In some implementations, while the mobile robot is mapping the area, the light source may output UV light to disinfect at least a portion of the area. When performing the 3D mapping, the mobile robot may detect objects (i.e., "hotspots") using one or more sensors that may include a bed, a chair, a table, a door handle, and the like, and may add them to the map. When the mapping of the area is complete and/or when the existing map is available, a processor of the mobile robot and/or computing device (e.g., server, remote platform or the like) communicatively connected to the mobile robot may simulate where the mobile robot moved within the area and emitted UV light within the area. In some implementations, the UV light may be emitted when the mobile robot is within the area, as the mobile robot moves within the area, before the mapping of the area, during the mapping of the area, and/or after the mapping of the area. In some implementations, the processor and/or computing device may plot the exposure of UV light onto the mapped area.

In some implementations, while the mobile robot operates (e.g., by moving or when stopped) within the area, the UV light output from the light source of mobile robot may be plotted to be represented on the mapped area, so that air, surfaces, and/or objects may be accounted for by the amount of UV light they received. That is, an exposure plot may be generated by a processor of the mobile robot and/or by a computing device communicatively coupled to the mobile robot, where the exposure plot may be based on the amount of UV light in each portion of the mapped environment.

In some implementations, one or more virtual tags may be located on the map, and/or one or more reference tags may be detected in the area. The one or more sensors of the robot may determine a change in state of the reference tags when UV light is emitted, and/or the processor and/or computing device may detect a change in state of the virtual tag based on the exposure plot, which would show whether the area that includes the virtual tag has been disinfected with UV light.

A report may be generated by the processor of the mobile robot and/or the computing device communicatively coupled to the mobile robot, where the report may include the surfaces, objects, and/or area that has been disinfected by the UV light. The report may include Key Performance Indicators (KPIs) such as the amount of time, the amount (i.e., number, percentage, or the like) of objects, surfaces, and the like that have not received enough UV light to effectively disinfect them, the amount of hotspots that have not received enough UV light to effectively disinfect them, the intensity of the UV light emission, and/or time of operation of the light source, or the like. The report may be used to verify whether a room, building, and/or area has been disinfected.

FIG. 1 shows an example method 10 of plotting a representation of ultraviolet (UV) light emitted from a light source of a mobile robot according to an implementation of the disclosed subject matter. At operation 12, a mobile robot (e.g., mobile robot 100 shown in FIGS. 2-5) may be moved by a drive system (e.g., drive system 108 shown in FIG. 2 and FIG. 5) within an area. The area may be a room, a building, a predetermined area of a geographical location, or the like.

At least one sensor (e.g., sensor 102, 102a, 102b, and/or 106 shown in FIGS. 2-5) of the mobile robot may be used to detect at least one of air within the area, a surface within the area, and/or an object within the area at operation 14. That is, the at least one of the air, surface, and/or object may be located within the area, and may include an environmental contaminant, such as infectious diseases, viruses, bacteria, and/or other types of harmful organic microorganisms.

The detecting in operation 14 may determine at least one of the air, the surface, and/or the object in a three dimensional space of the area, which may be mapped by a processor (e.g., controller 114 of the mobile robot 100 shown in FIG. 12) as a three-dimensional map as the mobile robot moves within the area. The detecting may include determining, using the processor and a signal from the at least one sensor, at least one hotspot that includes the at least one of the surface and the object. The at least one hotspot may be, for example, a chair, a seat, a bed, a sink, mirror, a door, a door handle, a wall, a floor, a ceiling, a shelf, and/or a surface of a table, or the like. In some implementations, the hotpot may be any object and/or surface defined in a memory that is communicatively coupled to the processor. For example, hotspots may be stored in memory 118 and/or fixed storage 120 shown in FIG. 12, and/or at server 140, database 150, and/or remote platform 160 show in FIG. 13.

At operation 16, the processor (e.g., controller 114 of the mobile robot 100 shown in FIG. 12) communicatively coupled to the at least one sensor, may map the area in three dimensions (3D) based on the detecting of at least one of the air, the surface, and the object as the mobile robot moves within the area. In some implementations, the mobile robot may use an existing 3D mapping of the area stored in a memory (e.g., memory 118 and/or fixed storage 120 of the mobile robot 100 shown in FIG. 12) of the mobile robot, and/or received by a communications interface (e.g., network interface 116 shown in FIG. 12) from a server (e.g., server 140 shown in FIG. 13), a database (e.g., database 150 shown in FIG. 13), and/or remote platform (e.g., remote platform 160 shown in FIG. 13) via a network (e.g., network 130 shown in FIG. 13) where the map may be stored. The map may indicate the locations of, for example, one or more objects and/or surfaces within the area. In some implementations, the map may be stored (e.g., memory 118 and/or fixed storage 120 of the mobile robot 100 shown in FIG. 12, and/or transmitted by a network interface 116 via network 103 to be stored in server 140, database 150, and/or remote platform 160 shown in FIG. 13) and used by the processor to control the drive system 108 to move the mobile robot. In some implementations, hotspots may be mapped.

At operation 18, a light source (e.g., light source 104 shown in FIGS. 2, 4, and 5) of the mobile robot may output ultraviolet (UV) light to disinfect at least a portion of the area, including the at least one of the air, the surface, and the object. The UV light may be emitted during at least one of: when the mobile robot is within the area, as the mobile robot moves within the area, before the mapping of the area, during the mapping of the area, and/or after the mapping of the area. The mobile robot may be used as part of a regular cleaning cycle of a room, building, or the like, and may prevent and/or reduce the spread of infectious diseases, viruses, bacteria, and other types of harmful organic microorganisms in the environment by breaking down their DNA-structure with UV light.

Figure 5:
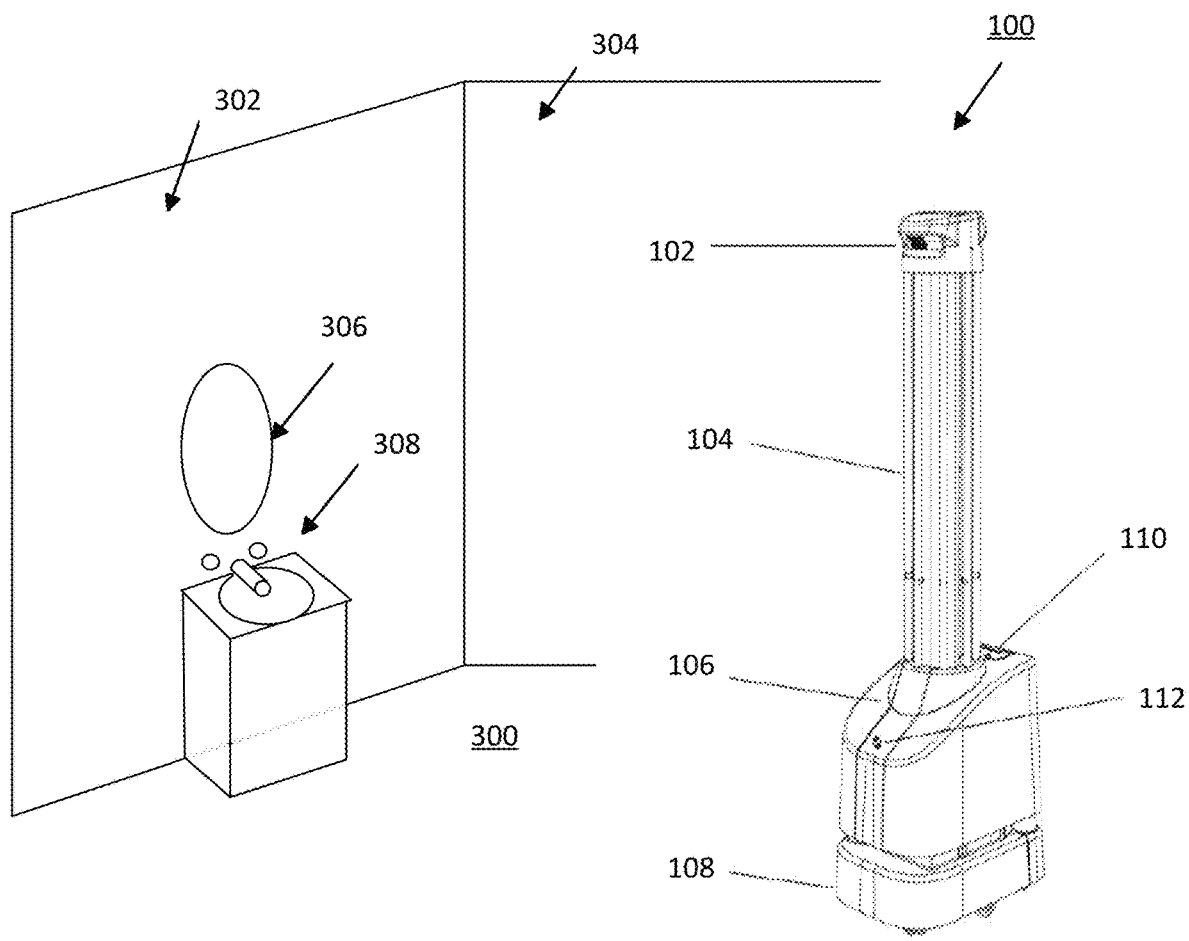
FIG. 5 shows an example of the mobile robot detecting surfaces and/or objects of an area to disinfect them with the UV light according to an implementation of the disclosed subject matter.

The mobile robot may detect air, surfaces, and/or objects of an area to disinfect them with the UV light according to an implementation of the disclosed subject matter as shown in FIG. 5. For example, sensors 102 and/or 106 of the mobile robot 100 may be used to detect surface 300 (e.g., a floor of the area), surface 302 and/or surface 306 (e.g., a wall of the area). The sensors 102 and/or 106 may be used to detect object 306 (e.g., a mirror) and/or object 308 (e.g., a sink). In some implementations, the processor may determine that one or more of the objects 306, 308 are hotspots. UV light may be emitted by the light source 104 to disinfect the surfaces 300, 302, 304 and/or the objects 306, 308. The map and the exposure plot may be generated by the processor of the mobile robot 100.

Figure 6:
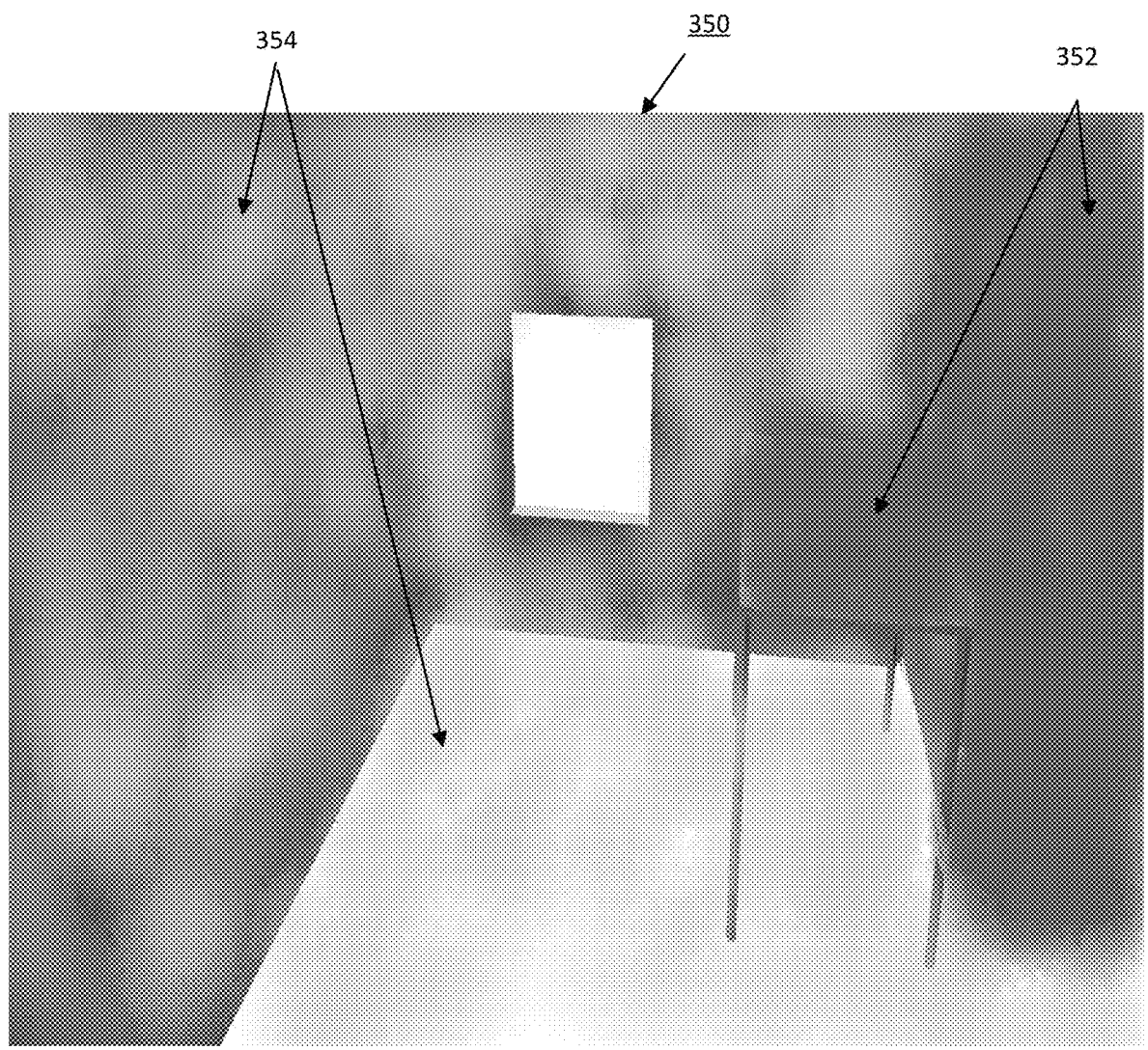
FIG. 6 shows an example plotting of a representation of the emission of the UV light in the area according to an implementation of the disclosed subject matter.

At operation 19, a representation of the emission of the UV light may be plotted by the processor onto the mapped area to generate an exposure plot. The representation is of the UV light emitted on at least one of the air, the surface, and the object in the area. An example of the exposure plot (e.g., exposure plot 350) is shown in FIG. 6. In the exposure plot 350, areas 352 may be areas that have been disinfected by UV light from the light source of the mobile robot. For example, the darker the areas 352 may be in the exposure plot 350, the more UV light that the surface and/or object may have received. Areas 354 may not have received as much UV light exposure as areas 352. For example, as shown in the exposure plot 350, the areas 354 are less dark than those of areas 352, which may indicate that they have received less UV light.

The mobile robot may reduce human error in cleaning an area, room, building, or the like by tracking the location and/or intensity (e.g., optical power of UV light) of light radiated, and determine which areas may need to be radiated and/or cleaned. The representation of the emission of the UV may be based on a light emission model used by the processor, where the UV light emitted is based on a square of a distance from the light source. The exposure plot (e.g., exposure plot 350 shown in FIG. 6) may be generated by the processor during the emission of the UV light or after disinfection of at least one of the air, the surface, and/or the object of the area. In some implementations, the plotting of the emitted UV light onto the mapped area may be performed after the area is mapped and disinfected.

Figure 12:
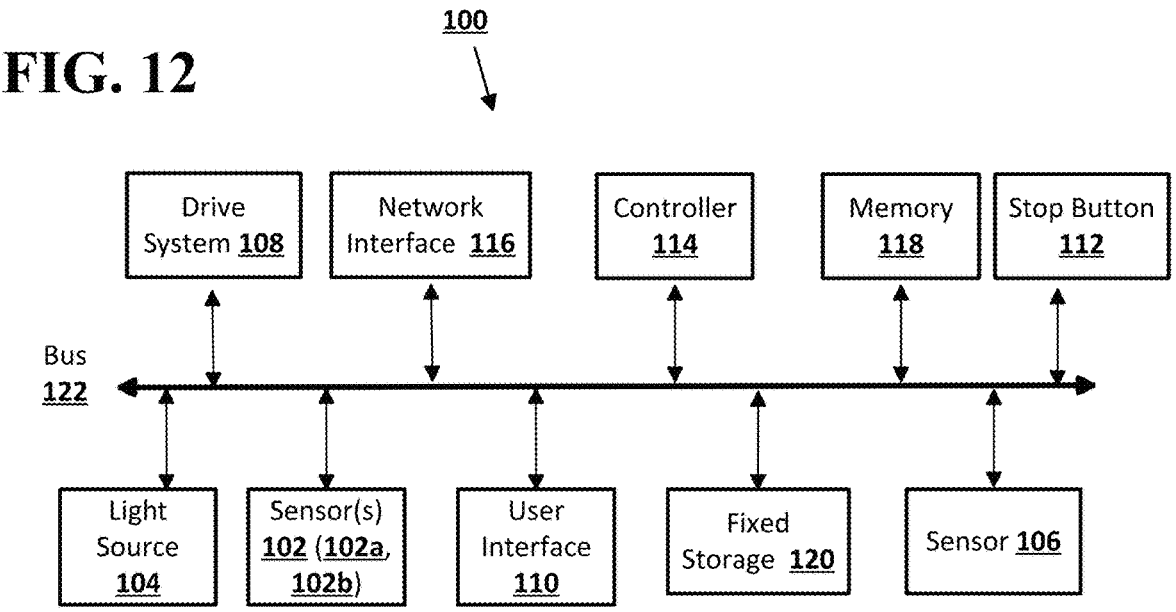
FIG. 12 shows an example configuration of the mobile robot of FIGS. 2-4 according to an implementation of the disclosed subject matter.
Figure 13:
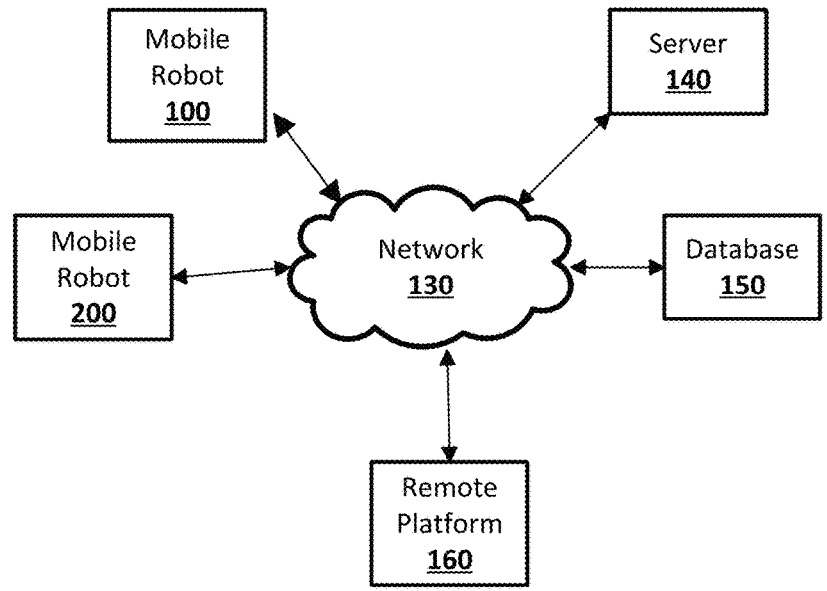
FIG. 13 shows a network configuration which may include a plurality of mobile robots according to implementations of the disclosed subject matter.

In some implementations, the method 10 may include transmitting a disinfection report using a communications interface of the mobile robot (e.g., network interface 116 of the mobile robot 100 shown in FIG. 12 may transmit via the network 130 shown in FIG. 13). An example disinfection report 400 is shown in FIG. 7. The disinfection report may include, for example, an amount of the area that has been disinfected based at least on the exposure plot, a number objects detected in the area, a percentage of the number of objects disinfected based on the detected number of objects and the exposure plot, a number of reference tags (and/or virtual tags) that have a changed stated based on exposure to the UV light, a path of the mobile robot moving in the area, and/or one or more deviations from a planned path of the mobile robot moving in the area, or the like.

As shown in the disinfection report 400 of FIG. 7, an amount of area disinfected by the mobile robot may be 100%, based on the exposure plot generated by the processor. In the example shown in FIG. 7, there may be seven (7) objects detected in the area by the one or more sensors of the mobile robot (e.g., sensors 102 and/or 106). The percentage of the number of objects disinfected may be 100%, which may be based on the number of objects detected, and the generated exposure plot (e.g., exposure plot 350 shown in FIG. 6). As shown in the disinfection report 400 of FIG. 7, there may be four (4) reference tags that have a changed state. That is, as described above, the reference tag (and/or virtual tags) may change from a first state to a second state when it receives UV light from the light source of the mobile robot. In some implementations, the disinfection report (e.g., disinfection report 400) may be stored in at least one of a storage device (e.g., memory 118 and/or fixed storage 120 shown in FIG. 12), a cloud storage device (e.g., at server 140 and/or remote platform 160 shown in FIG. 13), and/or a database system (e.g., database 150 shown in FIG. 13).

Figure 2:
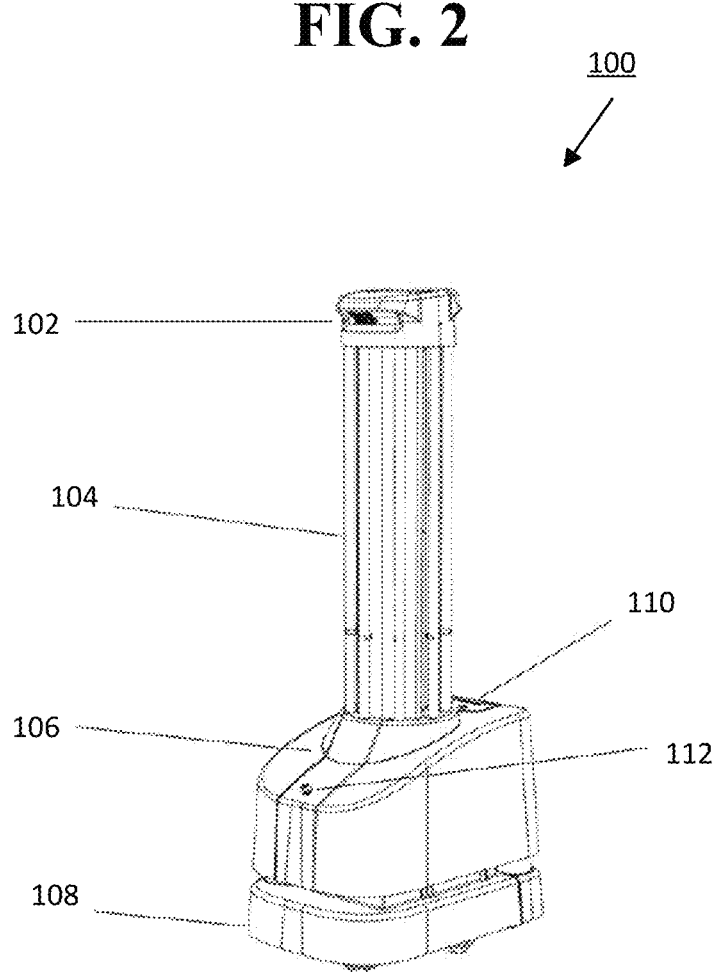
FIGS. 2-4 show a plurality of external views of the mobile robot having sensors to detect surfaces and objects in an area, and an ultraviolet (UV) light source to disinfect the air, objects, and/or surfaces in the area according to implementations of the disclosed subject matter.
Figure 3:
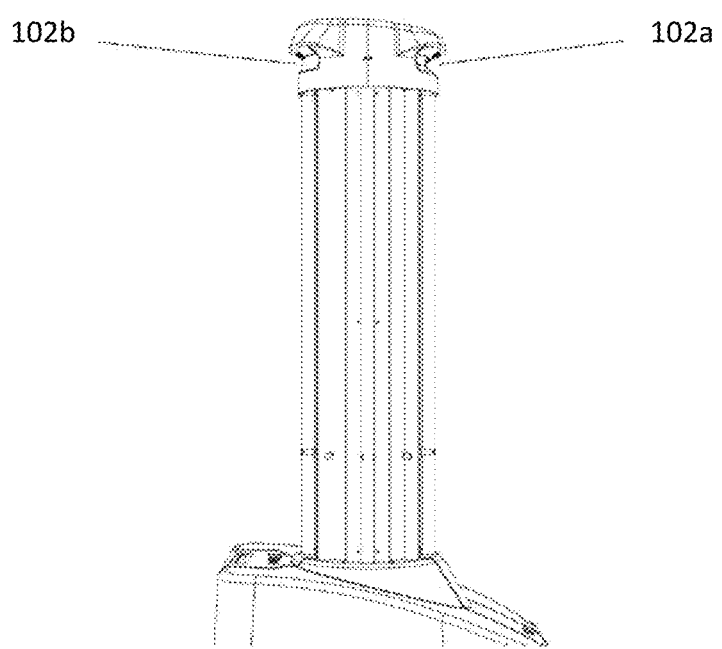
Figure 4:
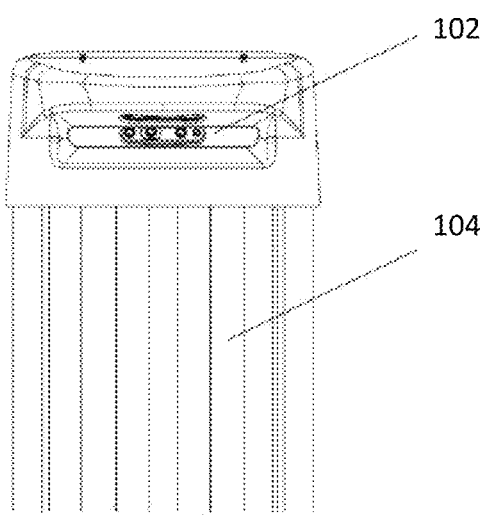

FIGS. 2-4 show a plurality of external views of a mobile robot 100 that includes sensors to detect surfaces and objects in an area, and an ultraviolet (UV) light source to disinfect the air, objects, and/or surfaces in the area according to implementations of the disclosed subject matter. The mobile robot 100 may include at least a first sensor 102 (shown as sensor 102a and 102b in FIG. 3), a light source 104 to output ultraviolet light, at least a second sensor 106, a drive system 108, a user interface 110, and/or a stop button 112. A controller (e.g., controller 114 shown in FIG. 12 and described below) may be communicatively coupled to the at least one first sensor 102, the light source 104, the at least one second sensor 106, the drive system 108, the user interface 110 and the stop button 112, may control the operations of the mobile robot 100.

The at least one first sensor 102 (including sensors 102a, 102b shown in FIG. 3) may determine at least one of an orientation of the mobile robot 100 (e.g., a direction that a front side and/or a first side of a robot is facing), a location of the mobile robot 100 (e.g., a location of the mobile robot 100 in an area), and/or when the light source 104 is within a predetermined distance of a surface and/or object in the area (e.g., surface 300, 302, and/or 304, and/or object 306, 308 shown in FIG. 5). In some implementations, the first sensor 102 may detect air, a surface, a reference tag, and/or objects that may be mapped by the mobile robot 100 and/or disinfected with UV light from the light source 104.

In some implementations, the at least one first sensor 102 may have a field of view of 70 degrees diagonally. The at least one sensor 102 may have a detection distance of 0.2-4 meters. As shown in FIGS. 2-4, the at least one first sensor 102 may be disposed over the light source 104.

The at least one first sensor 102 may include a first side sensor disposed on a first side of the mobile robot 100 and a second side sensor that may be disposed on a second side of the device. For example, as shown in FIG. 3, sensor 102a may be disposed on a first side (e.g., a front side) of the mobile robot 100, and sensor 102b may be disposed on a second side (e.g., a back side) of the mobile robot 100. Although sensors on two sides of the robot are shown in FIG. 3, there may be a plurality of sensors disposed on different sides of the mobile robot 102 to at least detect surfaces and/or objects. In some implementations, sensor 102a and/or sensor 102b may be disposed over the light source 104.

The light source 104 may be one or more bulbs, one or more lamps, and/or an array of light emitting diodes (LEDs) or organic light emitting diodes (OLEDs) to emit UV light (e.g., light having a wavelength of 10 nm-400 nm). The intensity (i.e., optical power output) may be controlled by the controller 114, which may also turn on or off a portion or all of the devices (e.g., bulbs, lamps, LEDs, OLEDs) of the light source 104. The light source may be controlled to emit UV light when the mobile robot is within an area, as the mobile robot moves within the area, before the mapping of the area, during the mapping of the area, and/or after the mapping of the area.

The at least one second sensor 106 may be communicatively coupled to the controller 114 shown in FIG. 12, and may be used to detect air, surfaces, and/or objects that may be mapped and/or disinfected with UV light from the light source 104. In some implementations, the at least one second sensor 106 may determine at least one of an orientation of the mobile robot 100 (e.g., a direction that a front side and/or a first side of a robot is facing), a location of the mobile robot 100 (e.g., a location of the mobile robot 100 in an area), and/or when the light source 104 is within a predetermined distance of a surface and/or object in the area (e.g., surface 300, 302, and/or 304, and/or object 306, 308 shown in FIG. 5).

In some implementations, the sensor 102, 106 may be a time-of-flight sensor, an ultrasonic sensor, a two-dimensional (2D) Light Detection and Ranging (LiDAR) sensor, a three-dimensional (3D) LiDAR sensor, and/or a radar (radio detection and ranging) sensor, a stereo vision sensor, 3D three camera, a structured light camera, or the like. The sensor 106 may have a field of view of 20-27 degrees. In some implementations, the sensor 106 may have a detection distance of 0.05-4 meters.

The mobile robot 100 may include a motor to drive the drive system 108 to move the mobile robot in an area, such as a room, a building, or the like. The drive system 108 may include wheels, which may be adjustable so that the drive system 108 may control the direction of the mobile robot 100.

In some implementations, the mobile robot 100 may include a base with the drive system 108, and the sensor 102, 106 may be disposed on the base.

The controller 114 may control and/or operate the mobile robot 100 in an operation mode which may be a manual mode, an autonomous mode, and/or a tele-operation mode. In the manual mode, the controller 114 may receive on or more control signals from the user interface 110 and/or the stop button 112. For example, a user may control the movement, direction, and/or stop the motion of the mobile robot 100 by making one or more selections on the user interface 110. The stop button 112 may be an emergency stop (ESTOP) button which may stop all operations and/or movement of the mobile robot 100 when selected. In some implementations, the controller 114 may receive at least one control signal via a network interface 116 (shown in FIG. 12) when operating when operating in the tele-operation mode. For example, the network interface may receive control signals via network 130 from server 140, database 150, and/or remote platform 160, as described below in connection with FIG. 13.

In some implementations, when the mobile robot 100 is moving in a direction, the sensor 102, 106 may detect a geometry of one or more surfaces (e.g., surfaces 300, 302, 304 shown in FIG. 5) and/or objects (e.g., objects 306, 308 shown in FIG. 5). The output of the at least one first sensor 102 may be, for example, a point cloud of the one or more objects in the path of the mobile robot 100. When the sensor 102 and/or sensor 106 is a stereo vision sensor, images from two sensors (i.e., where the two sensors may be part of the stereo vision sensor of the sensor 102 and/or sensor 106) within a known distance from one another distance may be captured at a predetermined point in time, and/or at predetermined time intervals with a global shutter. The global shutter may be configured so that the two sensors of the stereo vision sensor may capture images about simultaneously. One or more features (e.g., surfaces 300, 302, 304, and/or objects 306, 308 shown in FIG. 5) may be determined from the captured images, and be compared to one another to determine portions that are matching. As the focal length of the two sensors of the stereo vision sensor and the distance between the two sensors (e.g., about 6 cm) may be stored in memory 118 and/or fixed storage 120 (shown in FIG. 12), the controller 114 and/or the at least one first sensor 102 may use the captured images and the stored values to determine the distance from the sensor 102, 106 to the surfaces and/or objects, and may be used by the processor for mapping (as described above in connection with FIG. 1). In some implementations, the sensor 102, 106 may include at least one laser, LED, and/or OLED, to radiate one or more points on surfaces of objects, when the objects may be without identifying features (e.g., blank walls).

When detecting the surface and/or object, the sensor 102, 106 may be a time-of-flight (TOF) sensor. At least one photon of light may be output by the sensor 102, 106, and may be transmitted through the air. When the at least one photon of light radiates surface and/or an object, a portion of the light may be reflected by the surface and/or the object may return to a receiver portion of the sensor 102, 106. The sensor 106 may calculate the time between sending the at least one photon of light and receiving the reflection, and multiply this value by the speed of light in air, to determine the distance between the sensor 102, 106 and surface and/or object. This may be used to generate the map of the area that the mobile robot is operating within.

In some implementations, the method 10 shown in FIG. 1 may include calibrating an exposure calculation model for the processor of the mobile robot 100 for a selected calibration reference room. The exposure calculation model may determine an intensity and/or duration of UV light to emit from the light source 104 to disinfect air, surfaces, and/or objects within a room and/or area.

Figure 8:
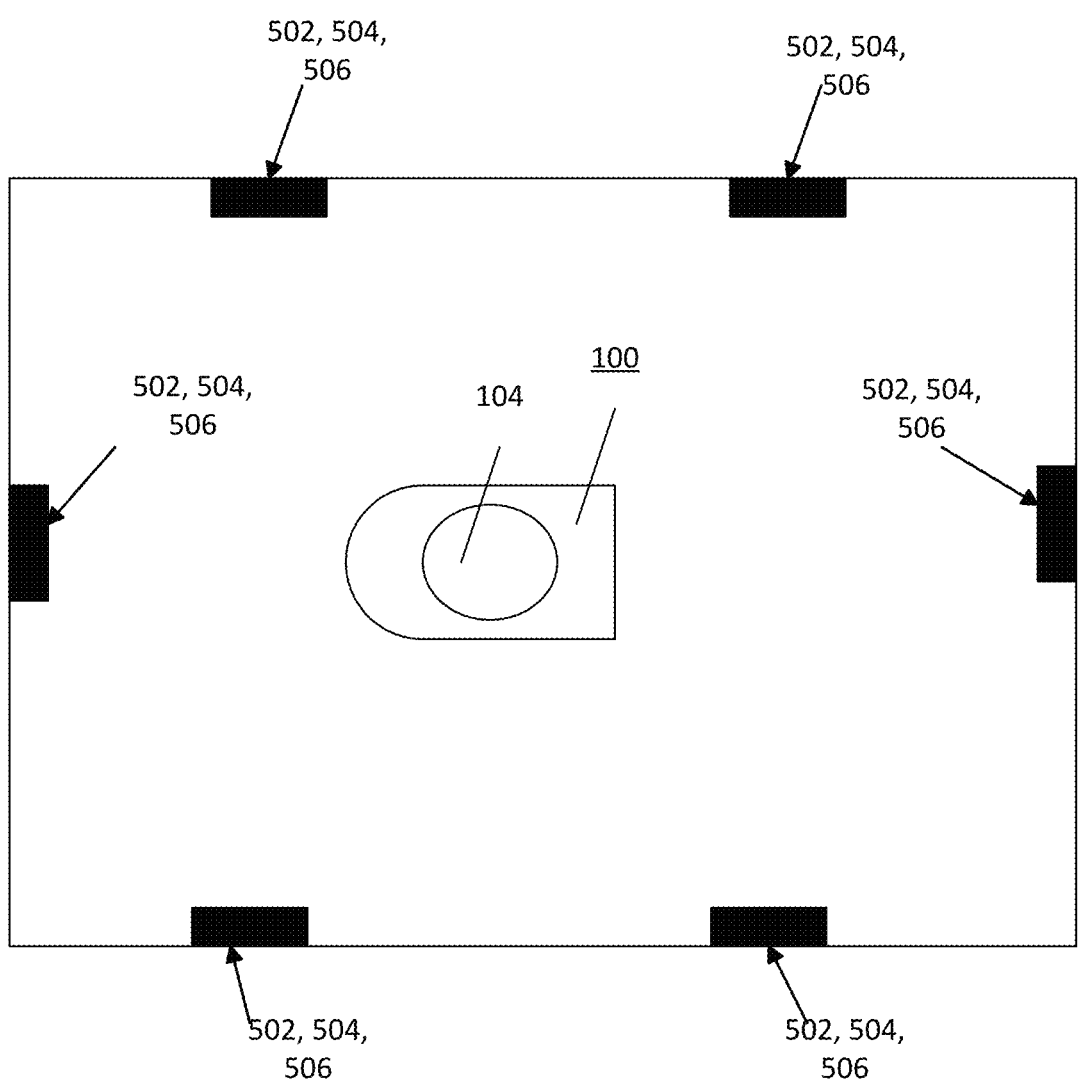
FIG. 8 shows an example of a selected calibration reference room for calibrating an exposure calculation model of the mobile robot according to an implementation of the disclosed subject matter.

FIG. 8 shows an example selected calibration reference room 500. Although the selected calibration reference room shown in FIG. 8 is rectangular, other selectable calibration reference rooms may include rooms having circular, oval, and/or other polygon shapes. The selected calibration reference room may include a plurality of sensors 502 to capture at least a portion of the UV light emitted by the light source 104 of the mobile robot 100, which may be used in generating a calibration signal, as discussed in detail below in connection with FIG. 9. In some implementations, the selected calibration reference room 500 may include reflective surfaces 504, which may optically reflect light emitted by the light source 104 of the mobile robot to at least one of the sensors 102, 106. The reflected light may be used to generate the calibration signal, as discussed below in connection with FIG. 10. In some implementations, the selected calibration reference room 500 may include reference tags 506, which may change state based on an exposure time and/or an exposure intensity of the UV light from the light source 104 of the mobile robot, as discussed below in connection with FIG. 11.

Figure 9:
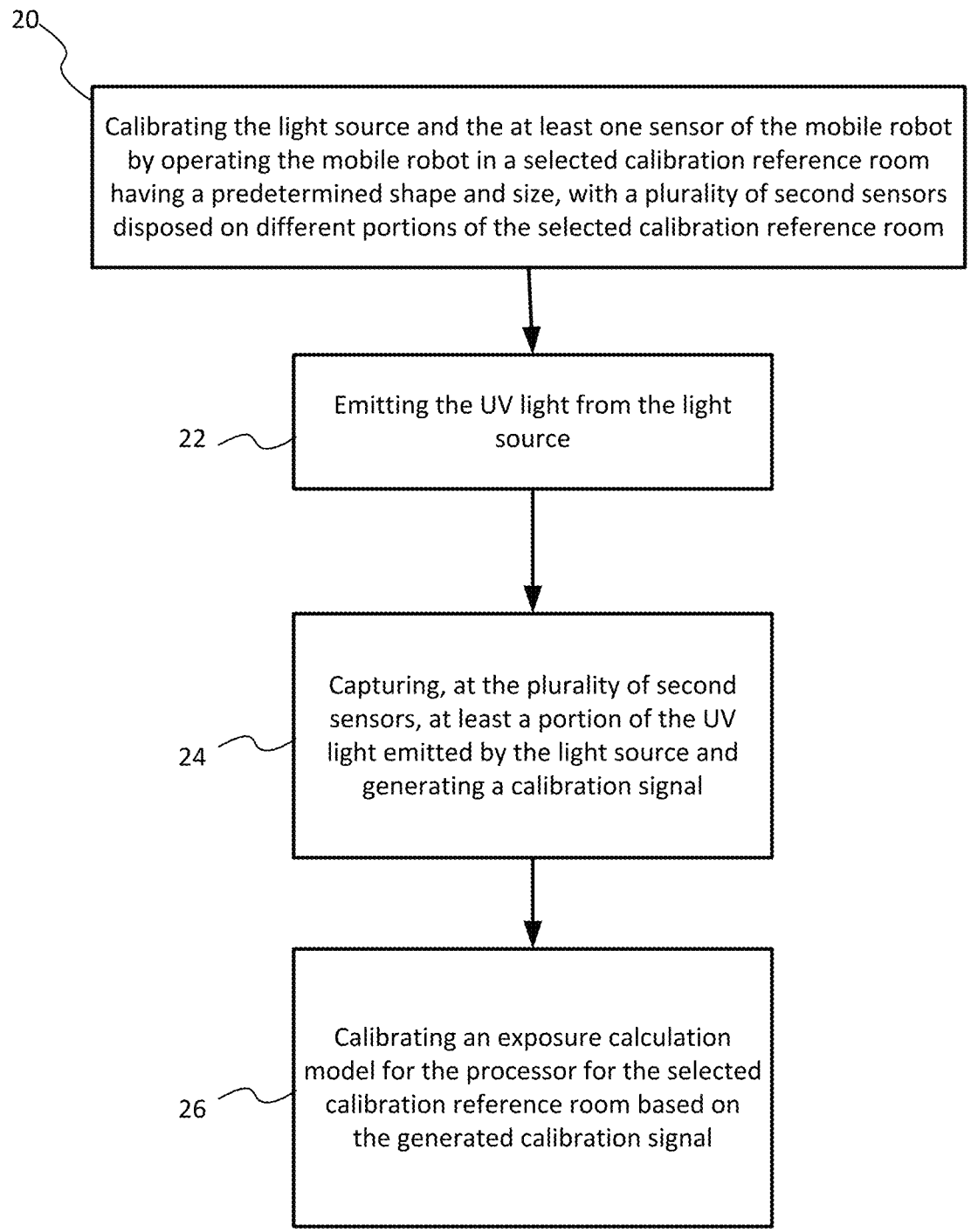
FIG. 9 shows an example calibration method using sensors in a selected calibration reference room according to an implementation of the disclosed subject matter.

An example calibration is shown in FIG. 9, where operation 20 calibrates the light source 104 and at least one sensor 102, 106 of the mobile robot 100 by operating the mobile robot 100 in a selected calibration reference room 500 having a predetermined shape and size, with sensors 502 may be disposed on different portions of the selected calibration reference room 500.

At operation 22, UV light may be emitted from the light source 104. One or more of the sensors 502 may capture at least a portion of the UV light emitted by the light source 104 and generate a calibration signal. In some implementations, the calibration signal may be transmitted from the sensors 502 to the network interface of the mobile robot 100 via the network 130. In some implementations, the signal provided by the sensors 502 may be used by the mobile robot to generate the calibration signal (e.g., using controller 114 shown in FIG. 12, and/or server 140 and/or remote platform 160 shown in FIG. 13). At operation 26, an exposure calculation model for the processor for the selected calibration reference room may be calibrated based on the generated calibration signal.

Figure 10:
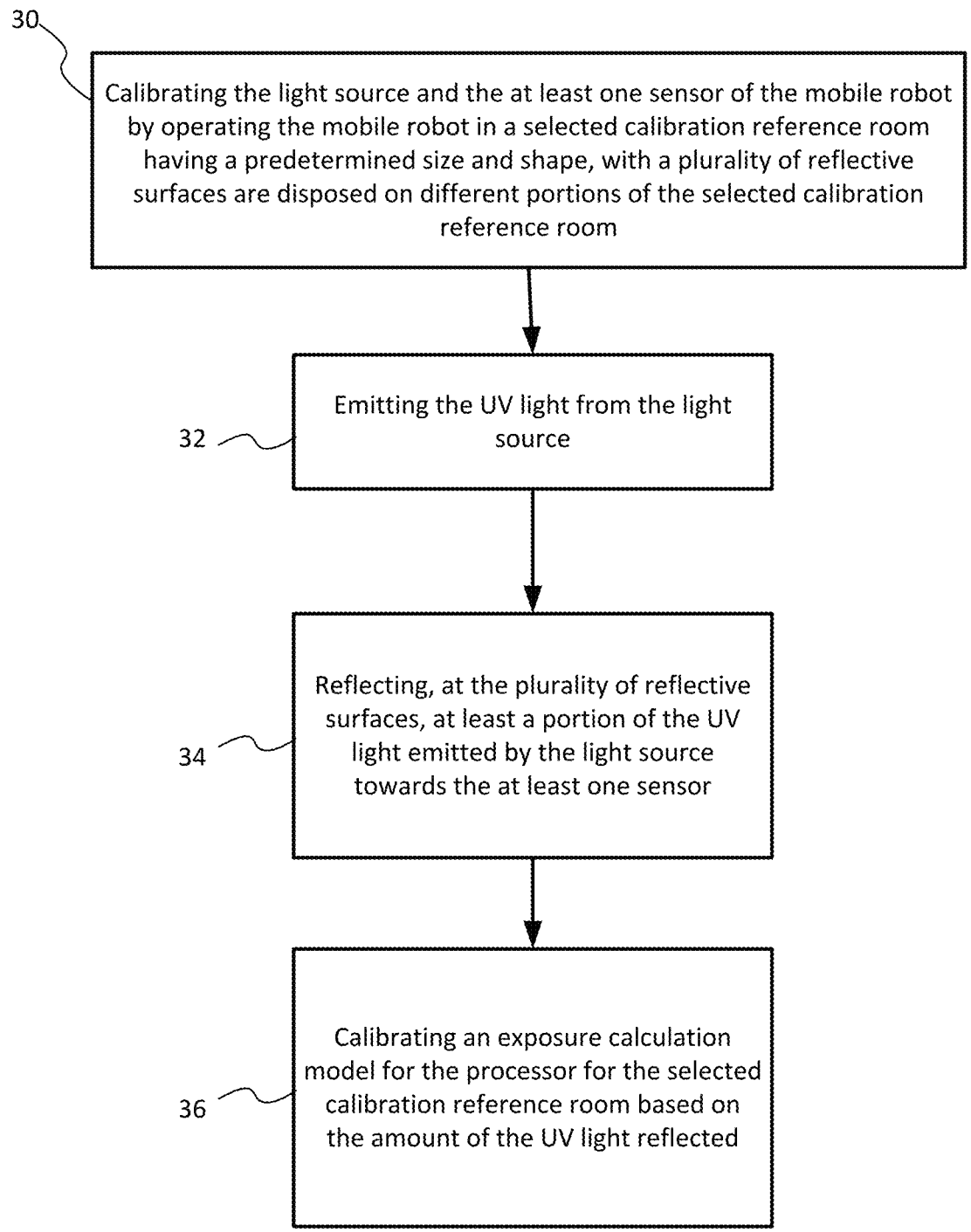
FIG. 10 shows an example calibration method using reflective surfaces in the selected calibration reference room according to an implementation of the disclosed subject matter.

Another example calibration is shown in FIG. 10, where operation 30 may calibrate the light source 104 and the sensor 102, 106 of the mobile robot by operating the mobile robot 100 in a selected calibration reference room 500 having a predetermined size and shape, with a plurality of reflective surfaces 504 are disposed on different portions of the selected calibration reference room 500.

At operation 32, the UV light may be emitted from the light source 104 of the mobile robot 100. At operation 34, one or more of the reflective surfaces 504 may reflect at least a portion of the UV light emitted by the light source 104 towards the sensor 102, 106. At operation 36, the exposure calculation model for the processor may be calibrated for the selected calibration reference room based on the amount of the UV light reflected and captured by the sensor 102, 106.

Figure 11:
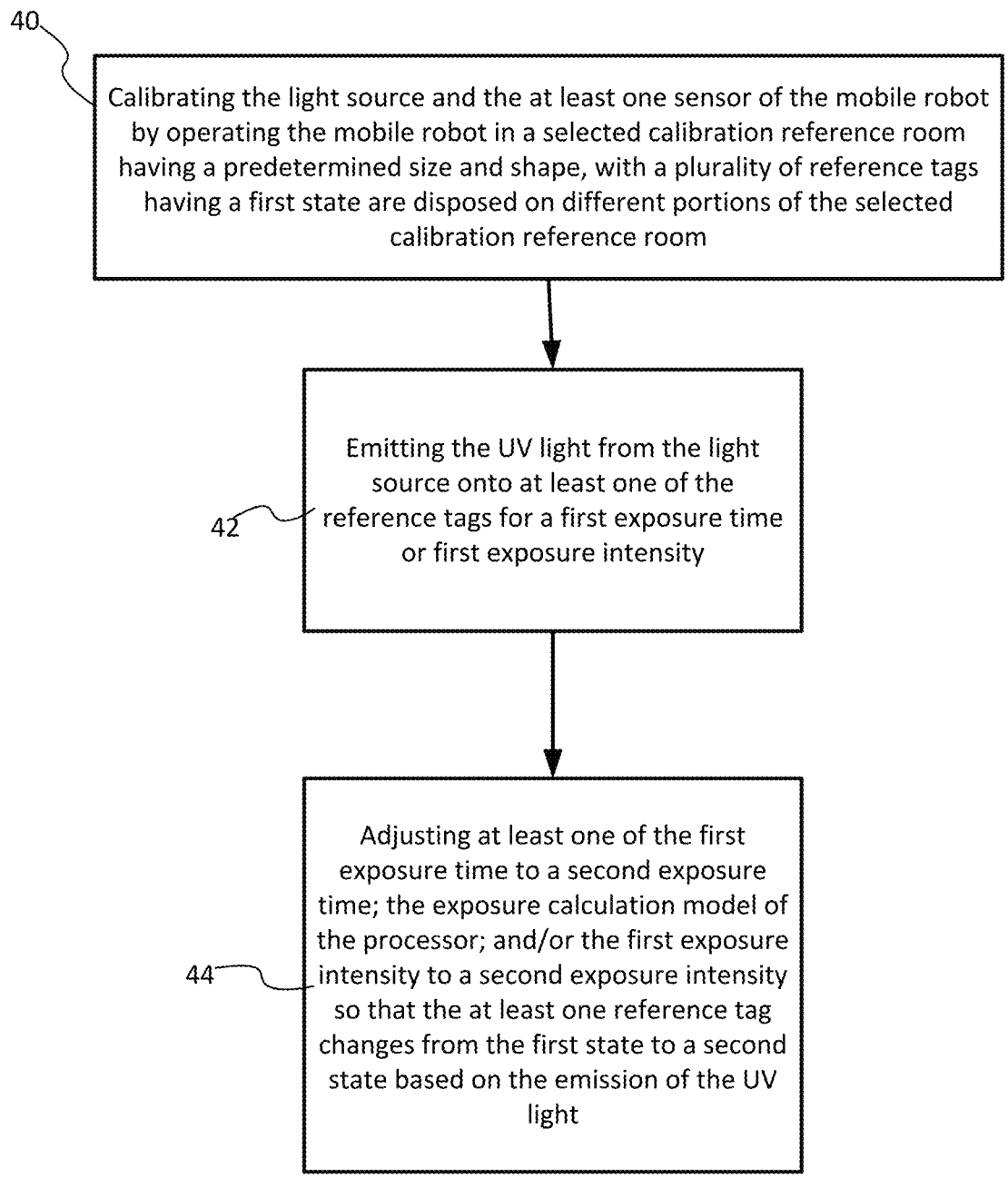
FIG. 11 shows an example calibration method using reference tags in the selected calibration reference room according to an implementation of the disclosed subject matter.

Another example calibration is shown in FIG. 11, where operation 40 may calibrate the light source 104 and the sensor 102, 106 of the mobile robot 100 by operating the mobile robot 100 in a selected calibration reference room 500 having a predetermined size and shape, with reference tags 506. The reference tag 506 may have a first state, and may be disposed on different portions of the selected calibration reference room 500.

At operation 42, the UV light may be emitted from the light source 104 onto at least one of the reference tags 506 for a first exposure time and/or a first exposure intensity. At operation 44, at least one of the following may be adjusted: the first exposure time to a second exposure time; the exposure calculation model of the processor; and/or the first exposure intensity to a second exposure intensity. The one or more adjustments may be made so that the at least one reference tag 506 changes from the first state to a second state based on the emission of the UV light. In some implementations, the adjustments may be used to calibrate the exposure calculation model.

For example, the amount of time that air, a surface, and/or an object (such as the reference tag) may be exposed to UV light from the light source 104 may be increased to change the state of the reference tag 506 from the first state to the second state, where the change in state may indicate that the area has been disinfected. In another example, the intensity of the UV light from the light source 104 may be adjusted so that the reference tag 506 changes from the first state to the second state.

FIG. 12 shows example components of the mobile robot 100 suitable for providing the implementations of the disclosed subject matter. The mobile robot 100 may include a bus 122 which interconnects major components of the mobile robot 100, such as the drive system 108, a network interface 116 operable to communicate with one or more remote devices via a suitable network connection, the controller 114, a memory 118 such as Random Access Memory (RAM), Read Only Memory (ROM), flash RAM, or the like, the stop button 112, the light source 104, the at least one first sensor 102, a user interface 110 that may include one or more controllers and associated user input devices such as a keyboard, touch screen, and the like, a fixed storage 120 such as a hard drive, flash storage, and the like, and the at least one second sensor 106.

The bus 122 allows data communication between the controller 114 and one or more memory components, which may include RAM, ROM, and other memory, as previously noted. Typically RAM is the main memory into which an operating system and application programs are loaded. A ROM or flash memory component can contain, among other code, the Basic Input-Output system (BIOS) which controls basic hardware operation such as the interaction with peripheral components. Applications resident with the mobile robot 100 are generally stored on and accessed via a computer readable medium (e.g., fixed storage 120), such as a solid state drive, hard disk drive, an optical drive, solid state drive, or other storage medium.

The network interface 116 may provide a direct connection to a remote server (e.g., server 140, database 150, and/or remote platform 160 shown in FIG. 13) via a wired or wireless connection (e.g., network 130 shown in FIG. 13). The network interface 116 may provide such connection using any suitable technique and protocol as will be readily understood by one of skill in the art, including digital cellular telephone, WiFi, Bluetooth®, near-field, and the like. For example, the network interface 116 may allow the mobile robot 100 to communicate with other computers via one or more local, wide-area, or other communication networks, as described in further detail below. The mobile robot may transmit data via the network interface to the remote server that may include a path of operation, the surfaces and/or areas radiated with UV light, and the like.

Many other devices or components (not shown) may be connected in a similar manner. Conversely, all of the components shown in FIG. 12 need not be present to practice the present disclosure. The components can be interconnected in different ways from that shown. Code to implement the present disclosure can be stored in computer-readable storage media such as one or more of the memory 118, fixed storage 120, or on a remote storage location.

FIG. 13 shows an example network arrangement according to an implementation of the disclosed subject matter. Mobile robot 100 described above, and/or a similar mobile robot 200 may connect to other devices via network 130.

The network 130 may be a local network, wide-area network, the Internet, or any other suitable communication network or networks, and may be implemented on any suitable platform including wired and/or wireless networks. The mobile robot 100 and/or mobile robot 200 may communicate with one another, and/or may communicate with one or more remote devices, such as server 140, database 150, and/or remote platform 160. The remote devices may be directly accessible by the mobile robot 100, 200 or one or more other devices may provide intermediary access such as where a server 140 provides access to resources stored in a database 150. The mobile robot 100, 200 may access remote platform 160 or services provided by remote platform 160 such as cloud computing arrangements and services. The remote platform 160 may include one or more servers 140 and/or databases 150.

More generally, various implementations of the presently disclosed subject matter may include or be embodied in the form of computer-implemented processes and apparatuses for practicing those processes. Implementations also may be embodied in the form of a computer program product having computer program code containing instructions embodied in non-transitory and/or tangible media, such as solid state drives, DVDs, CD-ROMs, hard drives, USB (universal serial bus) drives, or any other machine readable storage medium, such that when the computer program code is loaded into and executed by a computer, the computer becomes an apparatus for practicing implementations of the disclosed subject matter. Implementations also may be embodied in the form of computer program code, for example, whether stored in a storage medium, loaded into and/or executed by a computer, or transmitted over some transmission medium, such as over electrical wiring or cabling, through fiber optics, or via electromagnetic radiation, such that when the computer program code is loaded into and executed by a computer, the computer becomes an apparatus for practicing implementations of the disclosed subject matter. When implemented on a general-purpose microprocessor, the computer program code segments configure the microprocessor to create specific logic circuits.

In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions. Implementations may include using hardware that has a processor, such as a general purpose microprocessor and/or an Application Specific Integrated Circuit (ASIC) that embodies all or part of the techniques according to implementations of the disclosed subject matter in hardware and/or firmware. The processor may be coupled to memory, such as RAM, ROM, flash memory, a hard disk or any other device capable of storing electronic information. The memory may store instructions adapted to be executed by the processor to perform the techniques according to implementations of the disclosed subject matter.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A method comprising:
    moving, using a drive system, a mobile robot within an area;
    detecting, using at least one sensor of the mobile robot, at least one from the group consisting of: air within the area, a surface within the area, and an object within the area;
    mapping, using a processor communicatively coupled to the at least one sensor, the area in three dimensions (3D) based on the detecting of at least one of the air, the surface, and the object as the mobile robot moves within the area, or using an existing 3D mapping of the area stored in a memory communicatively coupled to the processor;
    emitting, using a light source of the mobile robot, ultraviolet (UV) light to disinfect at least a portion of the area, including the at least one of the air, the surface, and the object, wherein the emitting is performed during at least one selected from the group consisting of: when the mobile robot is within the area, as the mobile robot moves within the area, before the mapping of the area, during the mapping of the area, and after the mapping of the area; and
    plotting, using the processor, a representation of the emission of the UV light onto the mapped area to generate an exposure plot based on a light emission model of the processor, wherein the UV light emitted is based on a square of a distance from the light source detected by the at least one sensor, and wherein the representation is of the UV light emitted on at least one of the air, the surface, and the object in the area and includes an amount of UV light emitted in each portion of the mapped area.

2. The method of claim 1, wherein the exposure plot is generated during the emission of the UV light or after disinfection of at least one of the air, the surface, and the object of the area.

3. The method of claim 1, wherein the detecting determines at least one of the air, the surface, and the object in a three dimensional space of the area, which are mapped by the processor as a three-dimensional map as the mobile robot moves within the area.

4. The method of claim 1, wherein the detecting further comprises: determining, using the processor and a signal from the at least one sensor, at least one hotspot that includes the at least one of the surface and the object.

5. The method of claim 4, wherein the at least one hotspot is selected from a group consisting of: a chair, a seat, a bed, a sink, mirror, a door, a door handle, a wall, a floor, a ceiling, a shelf, a surface of a table, and any object or surface defined as the at least one hotspot in a memory that is communicatively coupled to the processor.

6. The method of claim 4, further comprising: mapping the at least one hotspot on the mapped area.

7. The method of claim 1, wherein the plotting of the emitted UV light onto the mapped area after the area is mapped and disinfected.

8. The method claim 1, further comprising:
    transmitting, using a communications interface of the mobile robot, a disinfection report.

9. The method claim 8, wherein the disinfection report includes at least one selected from the group consisting of: an amount of the area that has been disinfected based at least on the exposure plot; a number objects detected in the area; a percentage of the number of objects disinfected based on the detected number of objects and the exposure plot;
 a number of reference tags that have a changed state based on exposure to the UV light; a path of the mobile robot moving in the area; and one or more deviations from a planned path of the mobile robot moving in the area.

10. The method of claim 8, further comprising:
 storing the report in at least one selected from a group consisting of: a storage device, a cloud storage device, and a database system.

11. The method of claim 1, further comprising:
 calibrating an exposure calculation model for the processor for a selected calibration reference room.

12. The method of claim 11, wherein the calibrating further comprises: calibrating the light source and the at least one sensor of the mobile robot by operating the mobile robot in a selected calibration reference room having a predetermined shape and size, with a plurality of second sensors disposed on different portions of the selected calibration reference room, the calibrating including:
 emitting the UV light from the light source;
 capturing, at the plurality of second sensors, at least a portion of the UV light emitted by the light source and generating a calibration signal; and
 calibrating the exposure calculation model for the processor for the selected calibration reference room based on the generated calibration signal.

13. The method of claim 11, wherein the calibrating further comprises: calibrating the light source and the at least one sensor of the mobile robot by operating the mobile robot in a selected calibration reference room having a predetermined size and shape, with a plurality of reflective surfaces are disposed on different portions of the selected calibration reference room, the calibrating including:
 emitting the UV light from the light source;
 reflecting, at the plurality of reflective surfaces, at least a portion of the UV light emitted by the light source towards the at least one sensor; and
 calibrating the exposure calculation model for the processor for the selected calibration reference room based on the amount of the UV light reflected.

14. The method of claim 11, wherein the calibrating further comprises: calibrating the light source and the at least one sensor of the mobile robot by operating the mobile robot in a selected calibration reference room having a predetermined size and shape, with a plurality of reference tags having a first state are disposed on different portions of the selected calibration reference room, the calibrating including:
 emitting the UV light from the light source onto at least one of the reference tags for a first exposure time or first exposure intensity; and
 adjusting at least one from the group consisting of: the first exposure time to a second exposure time; the exposure calculation model of the processor; and the first exposure intensity to a second exposure intensity so that the at least one reference tag changes from the first state to a second state based on the emission of the UV light.

* * * * *